United States Patent
Dorman

(10) Patent No.: US 9,535,078 B2
(45) Date of Patent: Jan. 3, 2017

(54) THERMAL-MECHANICAL TESTING APPARATUS FOR ELECTRICALLY CONDUCTIVE SPECIMEN TESTING SYSTEMS AND METHOD FOR USE THEREOF

(71) Applicant: Dynamic Systems Inc., Poestenkill, NY (US)

(72) Inventor: Andrew Greg Dorman, Poestenkill, NY (US)

(73) Assignee: Dynamic Systems Inc., Poestenkill, NY (US)

( * ) Notice: Subject to any disclaimer, the term of this patent is extended or adjusted under 35 U.S.C. 154(b) by 461 days.

(21) Appl. No.: 14/083,001

(22) Filed: Nov. 18, 2013

(65) Prior Publication Data

US 2014/0140367 A1    May 22, 2014

Related U.S. Application Data

(60) Provisional application No. 61/728,023, filed on Nov. 19, 2012.

(51) Int. Cl.
*G01N 35/00* (2006.01)
*G01N 3/08* (2006.01)
*G01N 3/18* (2006.01)

(52) U.S. Cl.
CPC ............... *G01N 35/00* (2013.01); *G01N 3/08* (2013.01); *G01N 3/18* (2013.01);
(Continued)

(58) Field of Classification Search
CPC .............. G01N 3/00; G01N 3/08; G01N 3/18; G01N 35/00; G01N 2203/0019; G01N 2203/0226; G01N 2203/0246
(Continued)

(56) References Cited

U.S. PATENT DOCUMENTS 3,699,808 A * 10/1972 Ford ..................... G01N 3/38
                                                            73/575
5,092,179 A   3/1992 Ferguson
(Continued)

OTHER PUBLICATIONS

International Application No. PCT/US20131070586, International Search Report & Written Opinion, Mar. 28, 2014, 14 pages.

*Primary Examiner* — Lisa Caputo
*Assistant Examiner* — Nathaniel T Woodward
(74) *Attorney, Agent, or Firm* — Matthew J. Kinnier; Hoffman Warnick LLC

(57) ABSTRACT

A thermal-mechanical testing apparatus for use with an electrically conductive specimen testing system. In one embodiment, the apparatus includes a first compression anvil assembly, a mounting frame coupled to the first compression anvil assembly, and a second compression anvil assembly positioned opposite the first compression anvil assembly and the mounting frame. The first compression anvil assembly includes a mounting plate, a first compression anvil coupled to the mounting plate, and a heating current ground system coupled to the mounting plate. The mounting frame includes a set of conductive end plates, a set of insulating connectors connecting the conductive end plates, and a plurality of mounting components coupled to the insulating connectors. The mounting components are also coupled to the mounting plate. The second compression anvil assembly includes a conductive mounting plate, a second compression anvil coupled to the conductive mounting plate, and a heating current by-pass system coupled to the conductive mounting plate and one of the conductive end plates.

18 Claims, 11 Drawing Sheets

(52) U.S. Cl.
CPC ............... *G01N 2203/0019* (2013.01); *G01N 2203/0226* (2013.01); *G01N 2203/0246* (2013.01)

(58) Field of Classification Search
USPC ............ 374/4, 5, 29, 30, 44, 45, 46, 50, 51; 73/790, 794, 795, 798, 94, 818, 788, 766
See application file for complete search history.

(56) References Cited

U.S. PATENT DOCUMENTS

| | | | | |
|---|---|---|---|---|
| 5,176,028 | A * | 1/1993 | Humphrey | B29C 65/18 374/45 |
| 5,195,378 | A * | 3/1993 | Ferguson | G01N 3/10 73/790 |
| 5,481,086 | A * | 1/1996 | Ferguson | F27B 14/10 219/385 |
| 5,959,215 | A * | 9/1999 | Ono | G01N 3/36 73/789 |
| 5,993,058 | A * | 11/1999 | Rochard | H05B 6/105 219/632 |
| 6,422,090 | B1 | 7/2002 | Ferguson | |
| 7,363,822 | B2 * | 4/2008 | Lindeman | G01N 3/18 73/818 |
| 2005/0011275 | A1 * | 1/2005 | Ferguson | G01N 3/04 73/818 |
| 2006/0180577 | A1 | 8/2006 | Lindeman | |
| 2009/0314107 | A1 * | 12/2009 | Yakimoski | G01N 3/08 73/865.6 |
| 2013/0243029 | A1 * | 9/2013 | Ramrattan | G01N 25/00 374/46 |

* cited by examiner

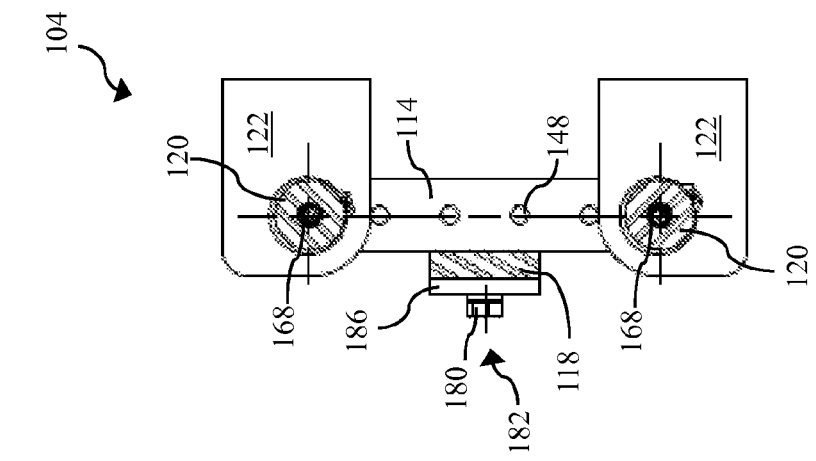
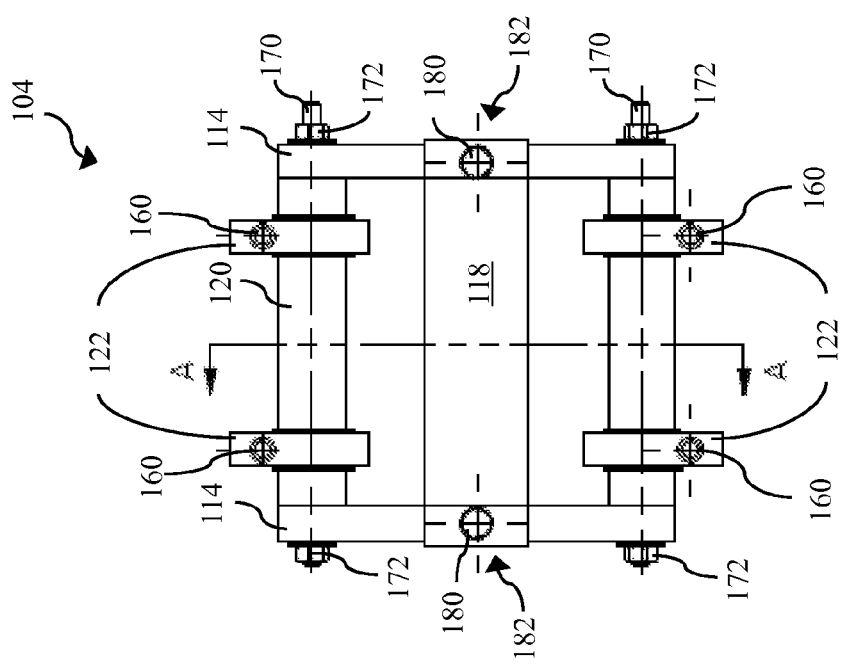
FIG. 7
FIG. 6

US 9,535,078 B2

THERMAL-MECHANICAL TESTING APPARATUS FOR ELECTRICALLY CONDUCTIVE SPECIMEN TESTING SYSTEMS AND METHOD FOR USE THEREOF

BACKGROUND OF THE INVENTION

1. Technical Field

The disclosure is related generally to electrical conductive specimen testing systems. More particularly, the disclosure is related to a thermal-mechanical testing apparatus for electrically conductive specimen testing systems, and a method for using the thermal-mechanical testing apparatus.

2. Related Art

Physical simulation of material processing involves the reproduction of the thermal and/or mechanical processes in the laboratory that the material is subjected to during an actual fabrication process or actual end use process. During the physical simulation, a sample of the actual material is used in a material testing machine or system capable of subjecting the sample material to the same thermal and/or mechanical processes that the material may undergo during a fabrication process or actual end use process. That is, the material testing machine or system simulates the material following the same thermal and/or mechanical profile that it would in the full scale fabrication process or end use process of the material. Typically, a sample of a material is heated and mechanically worked while various performance parameters of interest are measured and recorded by the material testing machine or system for later analysis. After the simulation is complete, the microstructure of the material may also be examined in order to verify that the material meets expected results and/or to understand the properties of the material produced during the physical simulation.

Depending on the capability of the material testing machine or system performing the simulation, the results can be extremely useful. These simulations have a variety of applications across the materials industry, including, Development of new processes, process improvements, and the discovery and implementation of new materials. When the physical simulation is accurate, the results can be readily transferred from the laboratory to the full size production process.

Two conventional fabrication processes simulated by material testing machines or systems are multi-stand rolling mills and multi-hit forging processes. These two simulated fabrication processes involve multiple-hit, high-speed deformation of the material during fabrication. The material testing machine or system used to simulate a multi-stand rolling mill and/or multi-hit forging typically includes two oppositely facing anvils capable of providing a compression force on a sample material positioned between the anvils. More specifically, the anvils of the testing machine or system are coupled to one or more hydraulic systems configured to allow the anvils to strike the sample material with a desired compression force and desired rate of deformation. Additionally, to properly simulate the multi-stand roll milling and/or multi-hit forging process, the material testing machine or system also provides a system for heating the sample material. More specifically, the sample material is heated during the simulation, to replicate the heating of the material during fabrication (e.g., multi-stand roll milling, multi-hit forging). The heating systems used in the simulation are typically a sub-system within material testing machine or system, or may be an independent system. These conventional heating systems typically heat only a small area (e.g., striking/compression area) of the sample material during simulation due to spatial constraints within the material testing machine or system and the need to rapidly heat and cool the material to replicate the process under study. That is, because of the limited testing space and need to heat and cool rapidly only a small area of the sample material can be heated without interfering with the simulation. In order to achieve accurate results during the simulation, it is imperative that the anvils strike or compress the heated area of the sample material.

BRIEF DESCRIPTION OF THE INVENTION

A thermal-mechanical testing apparatus for electrically conductive specimen testing systems, and a method for using the thermal-mechanical testing apparatus. In one embodiment, the thermal-mechanical testing apparatus includes: a first compression anvil assembly including: a mounting plate; a first compression anvil coupled to the mounting plate; and a heating current ground system coupled to the mounting plate; a mounting frame coupled to the first compression anvil assembly, the mounting frame including: a set of conductive end plates for positioning a first contact surface of a test specimen adjacent the first compression anvil of the first compression anvil assembly; a set of insulating connectors connecting the set of conductive end plates; and a plurality of mounting components coupled to the insulating connectors, the plurality of mounting components coupled to the mounting plate of the first compression anvil assembly; and a second compression anvil assembly positioned opposite the first compression anvil assembly and the mounting frame, the second compression anvil assembly including: a conductive mounting plate; a second compression anvil coupled to the conductive mounting plate, the second compression anvil positioned adjacent a second contact surface of the test specimen; and a heating current by-pass system coupled to the conductive mounting plate and one of the set of conductive end plates of the mounting frame.

A first aspect of the invention includes a thermal-mechanical testing apparatus having: a first compression anvil assembly including: a mounting plate; a first compression anvil coupled to the mounting plate; and a heating current ground system coupled to the mounting plate; a mounting frame coupled to the first compression anvil assembly, the mounting frame including: a set of conductive end plates for positioning a first contact surface of a test specimen adjacent the first compression anvil of the first compression anvil assembly; a set of insulating connectors connecting the set of conductive end plates; and a plurality of mounting components coupled to the insulating connectors, the plurality of mounting components coupled to the mounting plate of the first compression anvil assembly; and a second compression anvil assembly positioned opposite the first compression anvil assembly and the mounting frame, the second compression anvil assembly including: a conductive mounting plate; a second compression anvil coupled to the conductive mounting plate, the second compression anvil positioned adjacent a second contact surface of the test specimen; and a heating current by-pass system coupled to the conductive mounting plate and one of the set of conductive end plates of the mounting frame.

A second aspect of the invention includes a electrically conductive specimen testing system having: a housing; a first mounting shaft positioned within the housing on a first side; second mounting shaft positioned within the housing on a second side, opposite the first; and a thermal-mechanical testing apparatus coupled to the first mounting shaft and the second mounting shaft respectively, the thermal-mechanical testing apparatus including: a first compression anvil assembly coupled to the first mounting shaft, the first compression anvil assembly having: a mounting plate; a first compression anvil coupled to the mounting plate; and a heating current ground system coupled to the mounting plate; a mounting frame coupled to the first compression anvil assembly, the mounting frame having: a set of conductive end plates for positioning a first surface of a test specimen adjacent the first compression anvil of the first compression anvil assembly; a set of insulating connectors connecting the set of conductive end plates; and a plurality of mounting components coupled to the insulating connectors, the plurality of mounting components coupled to the mounting plate of the first compression anvil assembly; and a second compression anvil assembly coupled to the second mounting shaft, the second compression anvil assembly having: a conductive mounting plate; a second compression anvil coupled to the conductive mounting plate, the second compression anvil positioned adjacent a second surface of the test specimen; and a heating current by-pass system coupled to the conductive mounting plate and one of the set of conductive end plates of the mounting frame.

A third aspect of the invention includes a mounting frame for a test specimen having: a set of conductive end plates for receiving a respective end of the test specimen; a set of insulating connectors connecting the set of conductive end plates; and a plurality of mounting components coupled to the insulating connectors, the plurality of mounting components coupled to a mounting plate of a first compression anvil assembly.

A fourth aspect of the invention includes a method for performing a simulation on a test specimen. The method including: providing a thermal-mechanical testing apparatus, the thermal-mechanical testing apparatus including: a first compression anvil assembly including: a mounting plate; a first compression anvil coupled to the mounting plate; and a heating current ground system coupled to the mounting plate; a mounting frame coupled to the first compression anvil assembly, the mounting frame including: a set of conductive end plates for positioning a first contact surface of a test specimen adjacent the first compression anvil of the first compression anvil assembly; a set of insulating connectors connecting the set of conductive end plates; and a plurality of mounting components coupled to the insulating connectors, the plurality of mounting components coupled to the mounting plate of the first compression anvil assembly; and a second compression anvil assembly positioned opposite the first compression anvil assembly and the mounting frame, the second compression anvil assembly including: a conductive mounting plate; a second compression anvil coupled to the conductive mounting plate, the second compression anvil positioned adjacent a second contact surface of the test specimen; and a heating current by-pass system coupled to the conductive mounting plate and one of the set of conductive end plates of the mounting frame; continuously heating a contact area of the first contact surface and the second contact surface of the test specimen using the heating current by-pass system of the second compression anvil assembly; engaging the first compression anvil of the first compression anvil assembly against the first contact surface of the test specimen; and engaging the second compression anvil of the second compression anvil assembly against the second contact surface of the test specimen.

BRIEF DESCRIPTION OF THE DRAWINGS

These and other features of this invention will be more readily understood from the following detailed description of the various aspects of the invention taken in conjunction with the accompanying drawings that depict various embodiments of the invention, in which:

FIG. 6 shows a front view of a mounting frame including a test specimen as shown in FIG. 5, according to embodiments of the invention.

FIG. 7 shows a cross-section view along line A-A of the mounting frame including the test specimen as shown in FIG. 6, according to embodiments of the invention.

Figure 1:
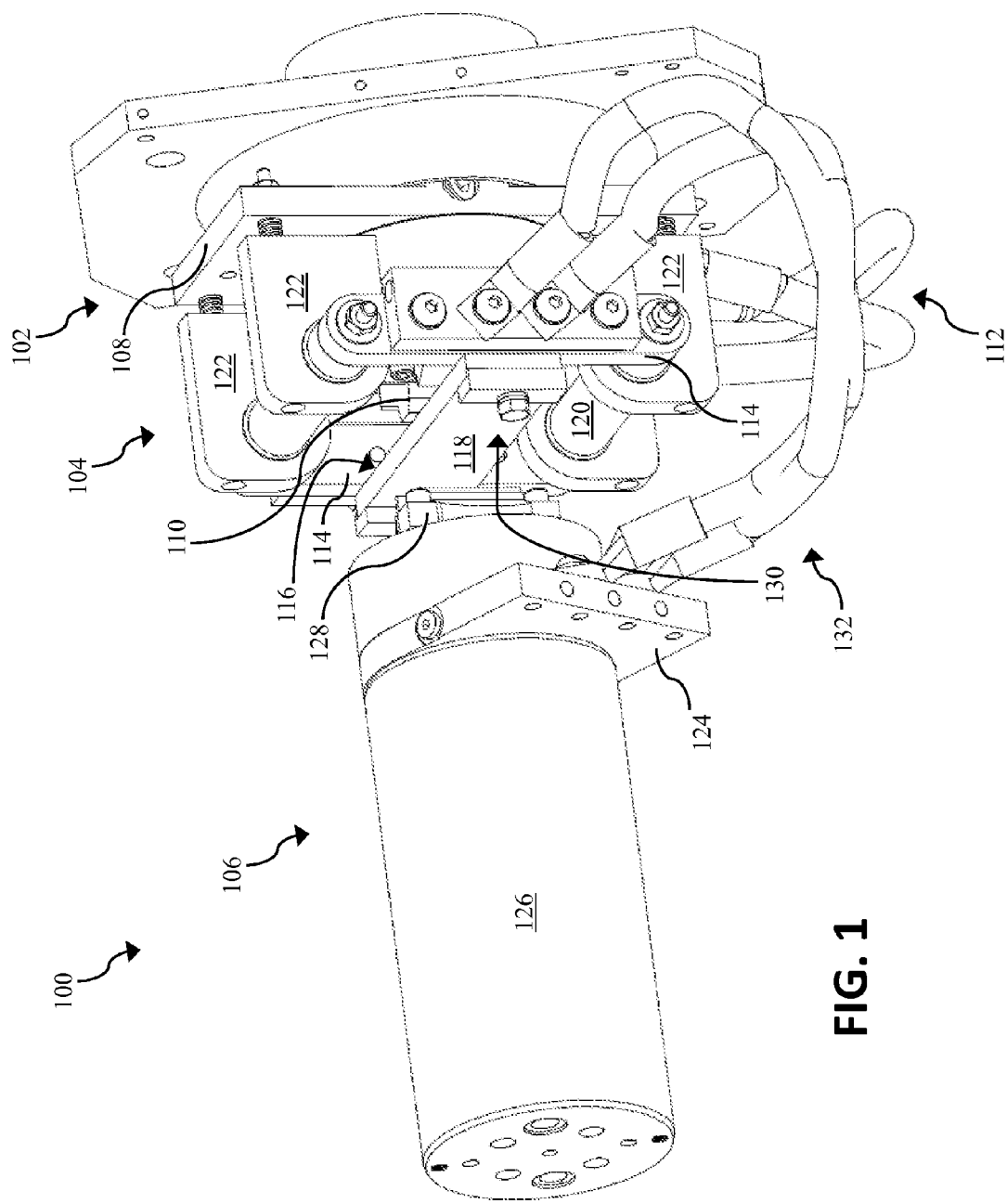
FIG. 1 shows a perspective view of a thermal-mechanical testing apparatus including a first compression anvil assembly, a mounting frame and a second compression anvil assembly, according to embodiments of the invention.

It is noted that the drawings of the invention are not necessarily to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As described herein, aspects of the invention relate to a electrically conductive specimen testing systems. Specifically, as described herein, aspects of the invention relate to a thermal-mechanical testing apparatus for electrically conductive specimen testing systems, and a method for using the thermal-mechanical testing apparatus.

Figure 2:
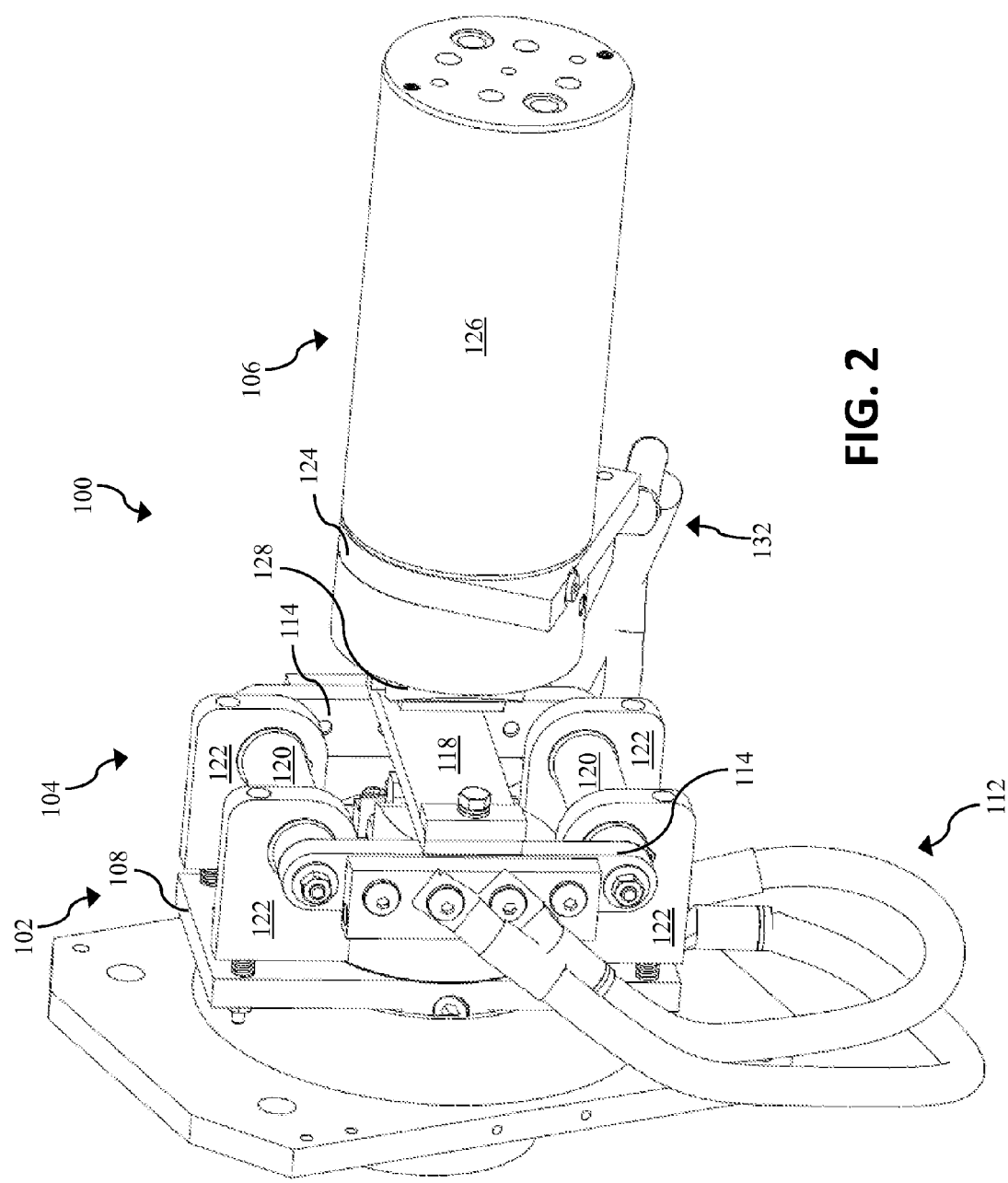
FIG. 2 shows an opposite perspective view of a thermal-mechanical testing apparatus including a first compression anvil assembly, a mounting frame and a second compression anvil assembly as shown in FIG. 1, according to embodiments of the invention.

Turning to FIGS. 1 and 2, opposite perspective views of a thermal-mechanical testing apparatus 100 are shown, including a first compression anvil assembly 102, a mounting frame 104 and a second compression anvil assembly 106 according to embodiments of the invention. A brief description of thermal-mechanical testing apparatus (TMTA) 100, and it's respective sub-components (e.g., first compression anvil assembly 102, mounting frame 104) is provided first, followed by a more detailed description of each of the sub-components of TMTA 100 with reference to FIGS. 3-12. In various embodiments, as shown in FIGS. 1 and 2, TMTA 100 may include first compression anvil assembly 102. As shown in FIGS. 1 and 2, first compression anvil assembly 102 may include a mounting plate 108, a first compression anvil 110 coupled to mounting plate 108, and heating current ground system 112 coupled to mounting plate 108.

As shown in FIGS. 1 and 2, TMTA 100 may also include mounting frame 104 coupled to first compression anvil assembly 102. Mounting frame 104 of TMTA 100 may include a set of conductive end plates 114 for positioning a first contact surface 116 of a test specimen 118 adjacent first compression anvil 110 of first compression anvil assembly 102. More specifically, as shown in FIGS. 1 and 2, test specimen 118 may be coupled to the set of conductive end plates 114, and may be positioned directly adjacent first compression anvil 110 of first compression anvil assembly 102.

In various embodiments, mounting frame 104 may also include a set of insulating connectors 120 connecting the set of conductive end plates 116. More specifically, as shown in FIGS. 1 and 2, the insulating connectors 120 may be coupled to each end of the set of conductive end plates 116 and may be positioned between the set of conductive end plates 116 at a length substantially similar to a length of test specimen 118. Mounting frame 104 of TMTA 100 may also include a plurality of mounting components 122 coupled to the set of insulating connectors 120. More specifically, as shown in FIGS. 1 and 2, mounting frame 104 may include four mounting components 122, such that two mounting components 122 are pivotally coupled to each of the insulating connectors 120. The plurality of mounting components 122 may also be coupled to mounting plate 108 of first compression anvil assembly 102. As discussed herein, by pivotally coupling the plurality of mounting components 122 to insulating connectors 120 and coupling the plurality of mounting components 122 to mounting plate 108, mounting frame 104, and more specifically, insulating connectors 120, the set of conductive end plates 114 and test specimen 118 may be free to rotate and/or pivot within mounting frame 104.

Also shown in FIGS. 1 and 2, TMTA 100 may include second compression anvil assembly 106 positioned opposite first compression anvil assembly 102 and mounting frame 104, respectively. That is, the second compression anvil assembly 106 may be positioned in alignment, and opposite first compression anvil assembly 102, such that mounting frame 104, and specifically, test specimen 118 may be positioned between the first compression anvil assembly 102 and the second compression anvil assembly 106. In an embodiment, as shown in FIGS. 1 and 2, the second compression anvil assembly 106 may include a conductive mounting plate 124. Conductive mounting plate 124 may be coupled to a shaft 126 of a electrically conductive specimen testing system (FIG. 13), as discussed herein. Second compression anvil assembly 106 may also include a second compression anvil 128 coupled to conductive mounting plate 124. Second compression anvil 128 may be positioned adjacent a second contact surface 130 of test specimen 118. As shown in FIGS. 1 and 2, the second compression anvil assembly 106 may include heating current by-pass system 132 coupled to conductive mounting plate 124 and one of the set of conductive end plates 114 of mounting frame 104.

Figure 3:
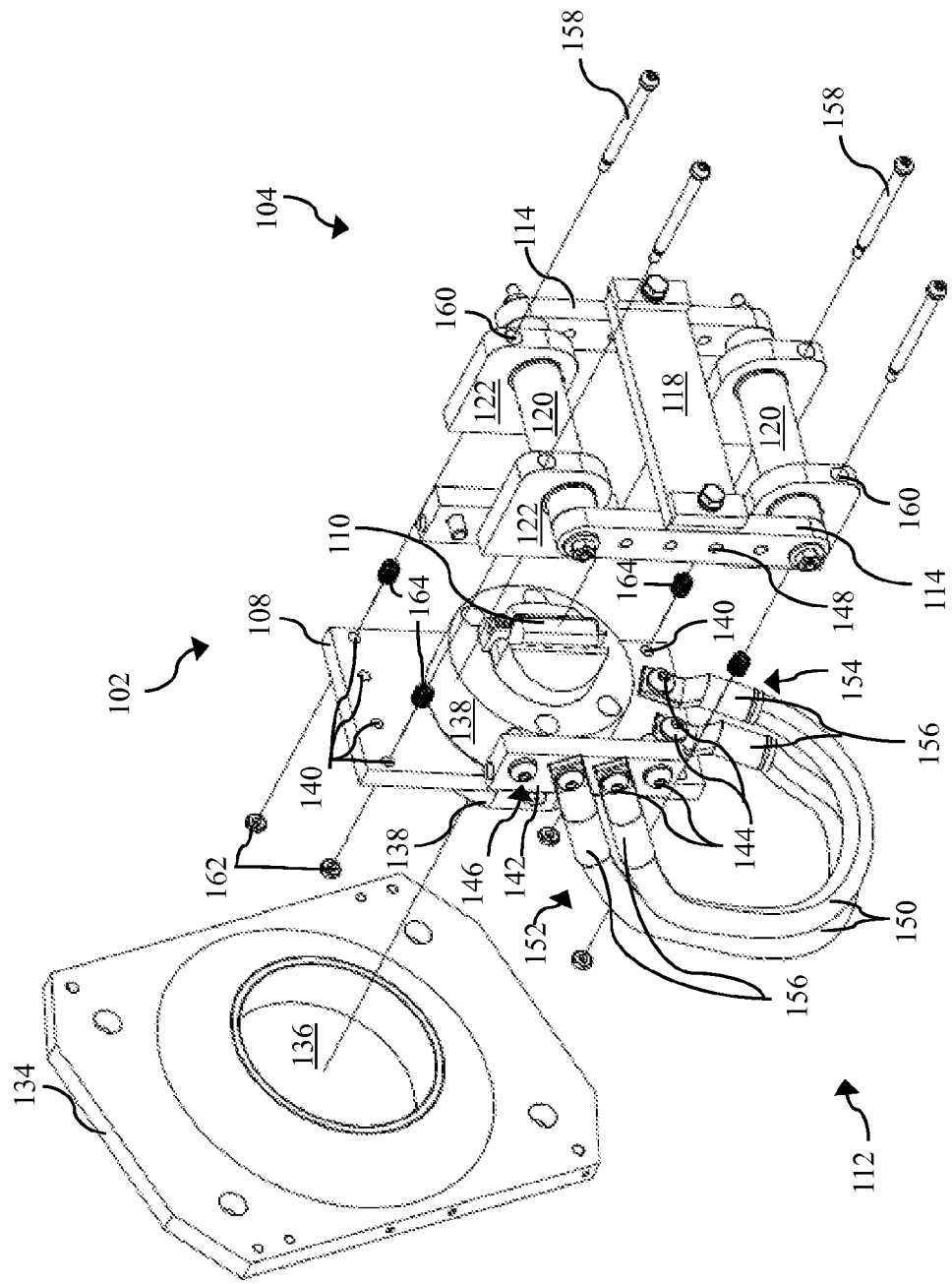
FIG. 3 shows a partially exploded perspective view of a mounting frame and a first compression anvil assembly including a mounting plate, a heating current ground system, according to embodiments of the invention.
Figure 4:
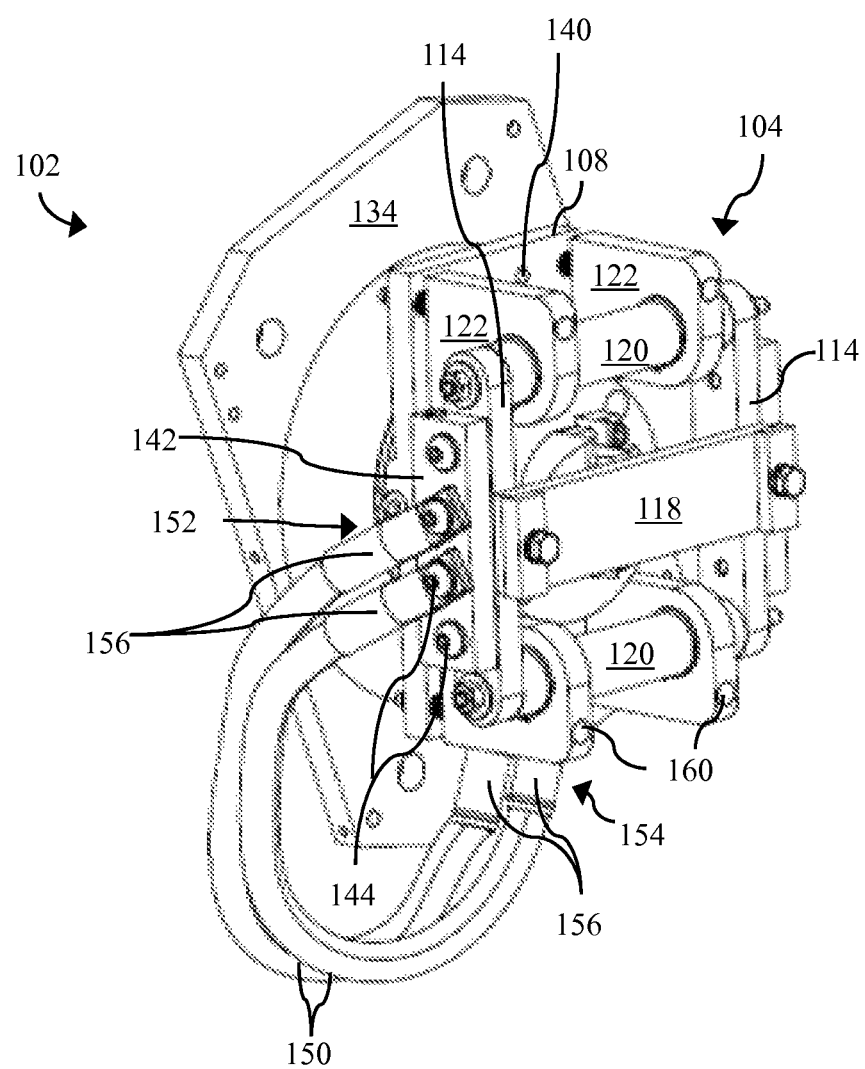
FIG. 4 shows a perspective view of a mounting frame and a first compression anvil assembly including a mounting plate and a heating current ground system as shown in FIG. 3, according to embodiments of the invention.

Turning to FIGS. 3 and 4, mounting frame 104 and the first compression anvil assembly 102 is shown, including mounting plate 108 and heating current ground system 112, according to embodiments of the invention. In an embodiment, as shown in FIGS. 3 and 4, first compression anvil 110 of first compression anvil assembly 102 may be configured as a water cooled compression anvil. As shown in FIGS. 3 and 4, first compression anvil assembly 102 may include a yoke bearing plate 134 positioned adjacent mounting plate 108. Yoke bearing plate 134 may include an opening 136 for positioning yoke bearing plate 134 circumferentially around a mounting shaft 138 including first compression anvil 110, and yoke bearing plate 134 may fixed within a housing of a electrically conductive specimen testing system (FIG. 13) utilizing TMTA 100. Yoke bearing plate 134 may also act as a guide and/or stabilizer for the first compression anvil assembly 102 coupled to an end of mounting shaft 138. That is, when a simulation is performed on test specimen 118, as discussed herein, yoke bearing plate 134 may substantially prevent first compression anvil assembly 102 from becoming misaligned (e.g., off center) from a potential deflection force of test specimen 118 during the simulation.

In various embodiments, as shown in FIGS. 3 and 4, mounting plate 108 may include a plurality of openings 140 extending through mounting plate 108. More specifically, mounting plate 108 may include the plurality of openings 140 positioned both above and below first compression anvil 110 of first compression anvil assembly 102. As shown in FIGS. 3 and 4, the plurality of openings 140 may couple mounting frame 104 to mounting plate 108, as discussed herein. Additionally, the plurality of openings 140 may couple a portion of heating current ground system 112 to mounting plate 108, as discussed herein. Mounting plate 108 may be made from any conventional conductive alloy, including, but not limited to, aluminum.

As shown in FIGS. 3 and 4, heating current ground system 112 of first compression anvil assembly 102 may include a ground plate 142 coupled to one of the set of conductive end plates 114 of mounting frame 104. More specifically, as shown in FIG. 4, ground plate 142 may be coupled to one of the set of conductive end plates 114 by positioning a screw 144 within one of a plurality of apertures 146 formed on ground plate 142 and one of a plurality of apertures 148 formed on the set of conductive end plates 114. That is, the plurality of apertures 146 of ground plate 142 may be concentrically aligned with the plurality of apertures 148 of the set of conductive end plates 114. Ground plate 142 may be coupled to one of the set of conductive end plates 114 to form an electric current connection between ground plate 142 and the set of conductive end plates 114, as discussed herein. That is, as shown in FIG. 4, ground plate 142 of heating current ground system 112 may substantially contact test specimen 118 to provide an electric current connection between ground plate 142 and test specimen 118. In an alternative embodiment, ground plate 142 may be coupled to one of the set of conductive end plates 114 by any conventional mechanical coupling technique, e.g., fastening, welding, brazing, bolting, etc.

Heating current ground system 112 of first compression anvil assembly 102 may also include at least one conductive cable 150 having a first end 152 coupled to ground plate 142, and a second end 154 coupled to mounting plate 108 of first compression anvil assembly 102. More specifically, as shown in FIGS. 3 and 4, first end 152 and second end 154 of the at least one conductive cable 150 may include a crimp lug 156 for coupling first end 152 to ground plate 142 and second end 154 to mounting plate 108. As shown in FIGS. 3 and 4, screws 144 may be positioned within crimp lug 156 for coupling first end 152 and second end 154 to the respective components (e.g., ground plate 142, mounting plate 108) of first compression anvil assembly 102. The at least one conductive cable 150, as shown in FIGS. 3 and 4, may be coupled to ground plate 142 and mounting plate 108 to form an electric current connection between ground plate 142 and mounting plate 108. More specifically, as discussed herein, the at least one conduction cable 150 may be coupled to ground plate 142 and mounting plate 108 in order to provide an electric current ground for TMTA 100 (FIGS. 1 and 2). The at least one conduction cable 150 may include a flexible copper cable capable of transferring a heating current through TMTA 100, as discussed herein. In an alternative embodiment, the at least one conductive cable 150 may be coupled ground plate 142 and/or mounting plate 108 by any conventional mechanical coupling technique, e.g., fastening, welding, brazing, bolting, etc.

In various embodiments, as shown in FIGS. 3 and 4, mounting frame 104 may be coupled to first compression anvil assembly 102. More specifically, as shown in FIGS. 3 and 4, the plurality of mounting components 122 of mounting frame 104 may be coupled to mounting plate 108 of first compression anvil assembly 102. As shown in FIG. 3, the plurality of mounting components 122 may be coupled to mounting plate 108 by positioning a shoulder screw 158 concentrically through an opening 160 extending through each of the plurality of mounting components 122 and the plurality of openings 140 of mounting plate 108. A nut 162 may be coupled to an end of shoulder screw 158 to maintain shoulder screw 158 within the plurality of mounting components 122 and mounting plate 108. In an embodiment, as shown in FIGS. 3 and 4, a compression spring 164 may be positioned between each of the plurality of mounting components 122 and mounting plate 108. That is, shoulder screw 158 may be positioned concentrically through compression spring 164, as well as opening 160 and opening 140, such that compression spring 164 may substantially separate mounting frame 104 and first compression anvil assembly 102. More specifically, compression spring 164 may apply a force on the plurality of mounting components 122 to move test specimen 118 coupled to mounting frame 104 away from first compression anvil 110 of first compression anvil assembly 102. The distance of separation between mounting frame 104 and first compression anvil assembly 102 created by compression spring 164 may be adjusted by one of tightening or loosening nut 162 coupled to shoulder screw 158. As discussed herein, by separating mounting frame 104 and first compression anvil assembly 102, and specifically, test specimen 118 and first compression anvil 110, test specimen 118 may be heated prior to first compression anvil 110 coming in contact with test specimen 118 during a simulation performed on test specimen 118.

Figure 5:
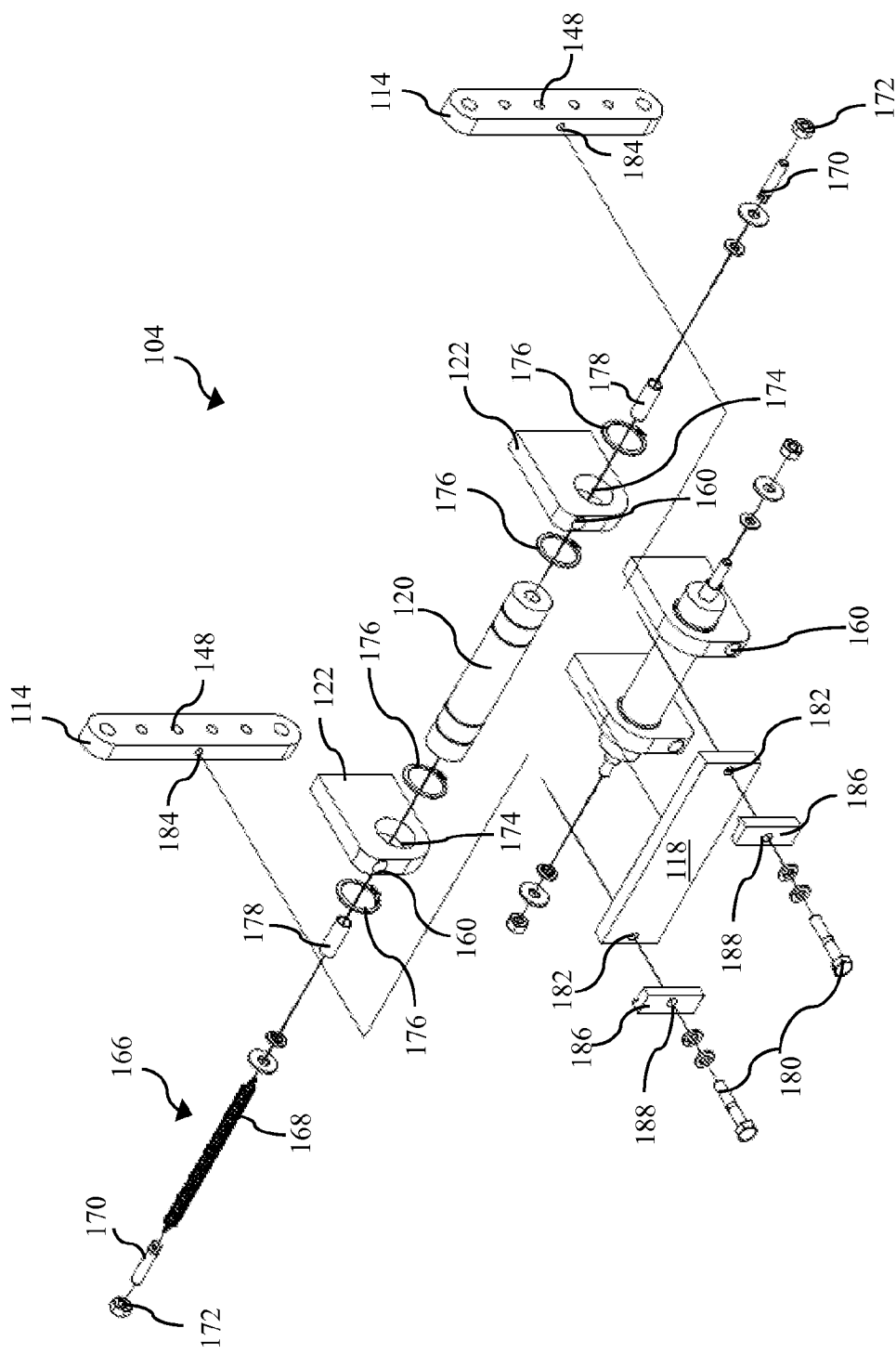
FIG. 5 shows a partially exploded perspective view of a mounting frame including a test specimen, according to embodiments of the invention.
Figure 8:
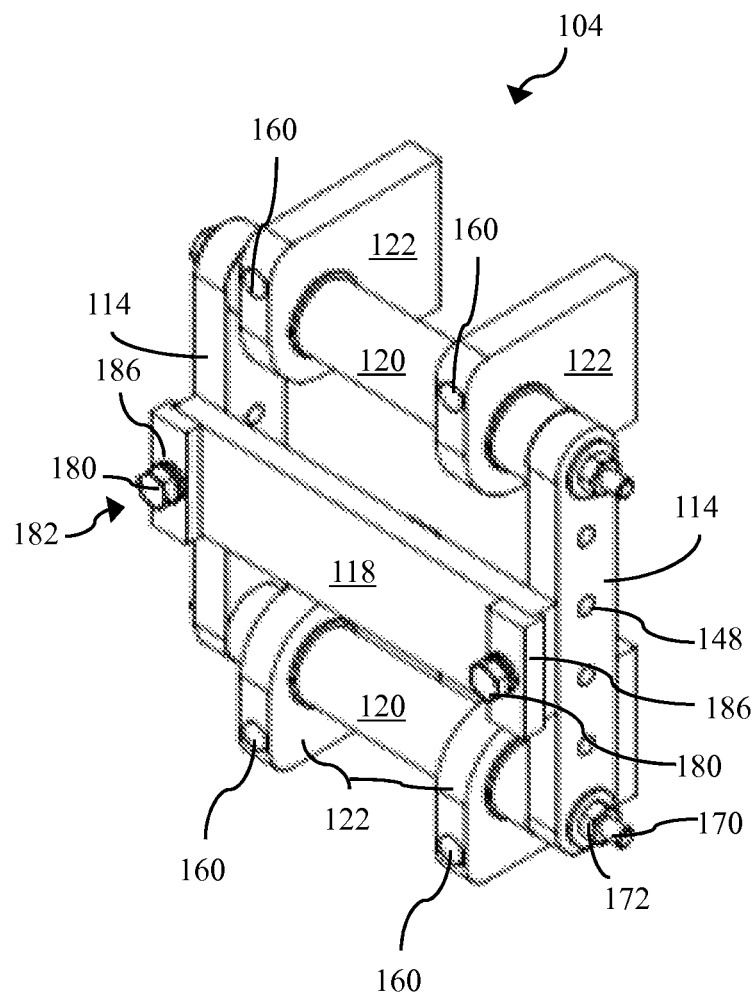
FIG. 8 shows a perspective view of a mounting frame including a test specimen as shown in FIG. 5, according to embodiments of the invention.
Figure 9:
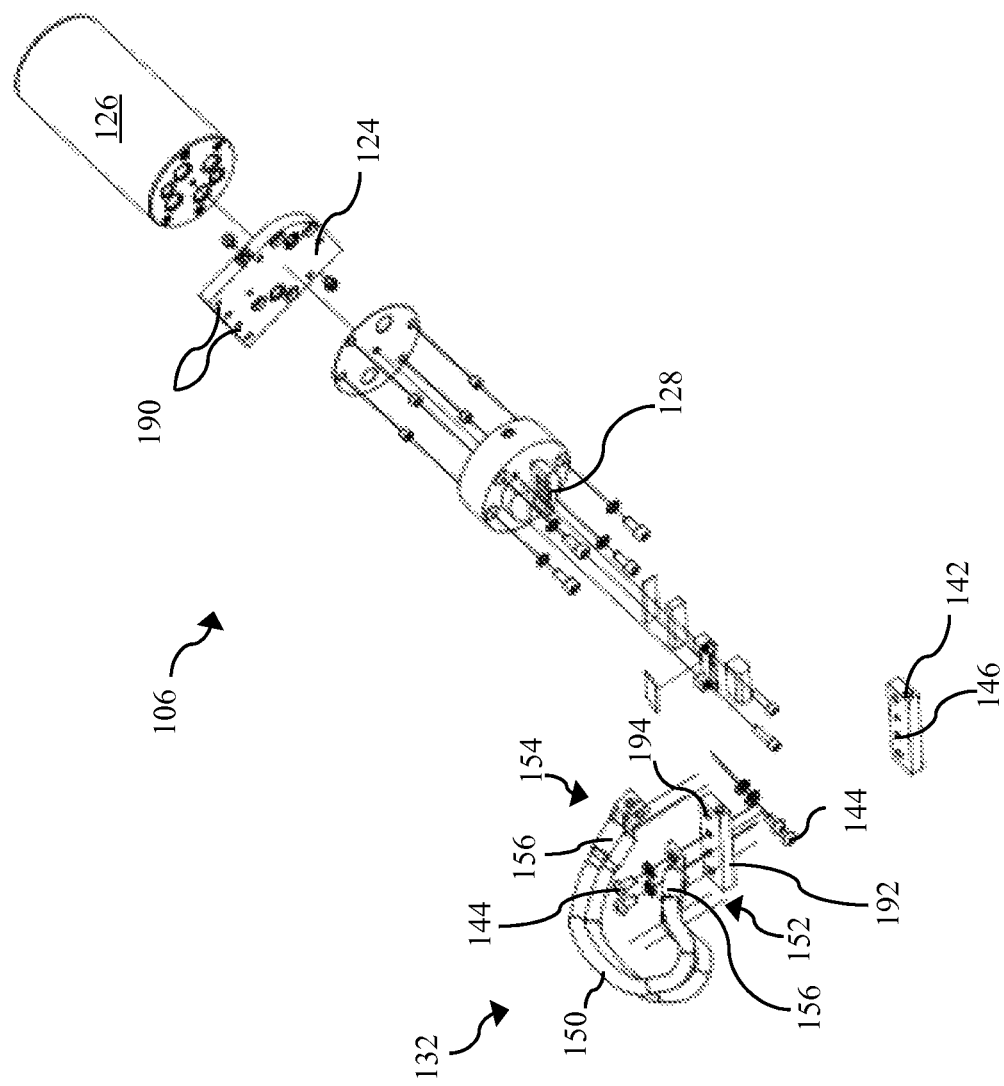
FIG. 9 shows an exploded perspective view of a second compression anvil assembly including a heating current by-pass system, according to embodiments of the invention.
Figure 10:
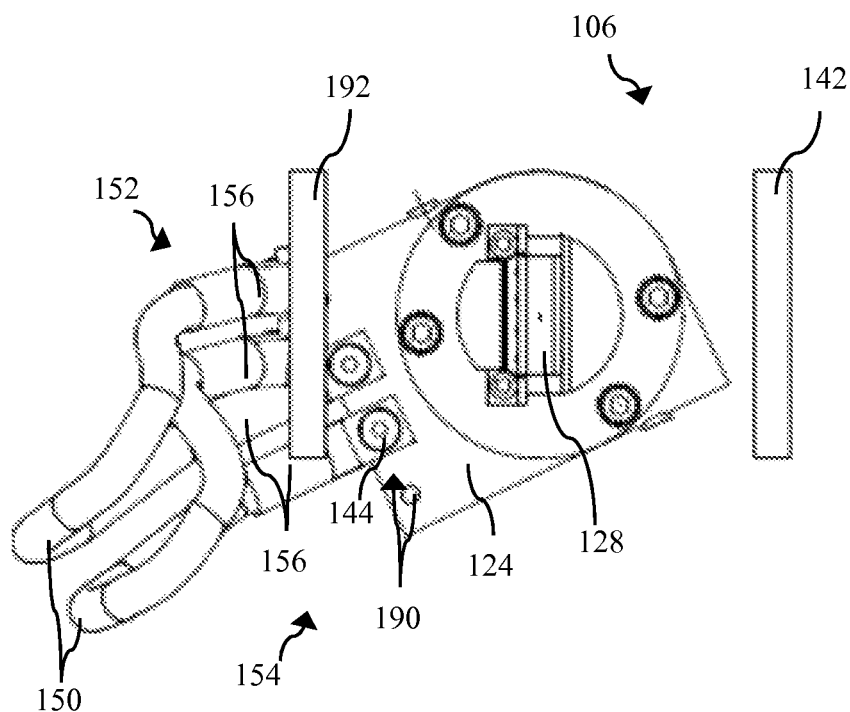
FIG. 10 shows a front view of a second compression anvil assembly including a heating current by-pass system as shown in FIG. 9, according to embodiments of the invention.
Figure 11:
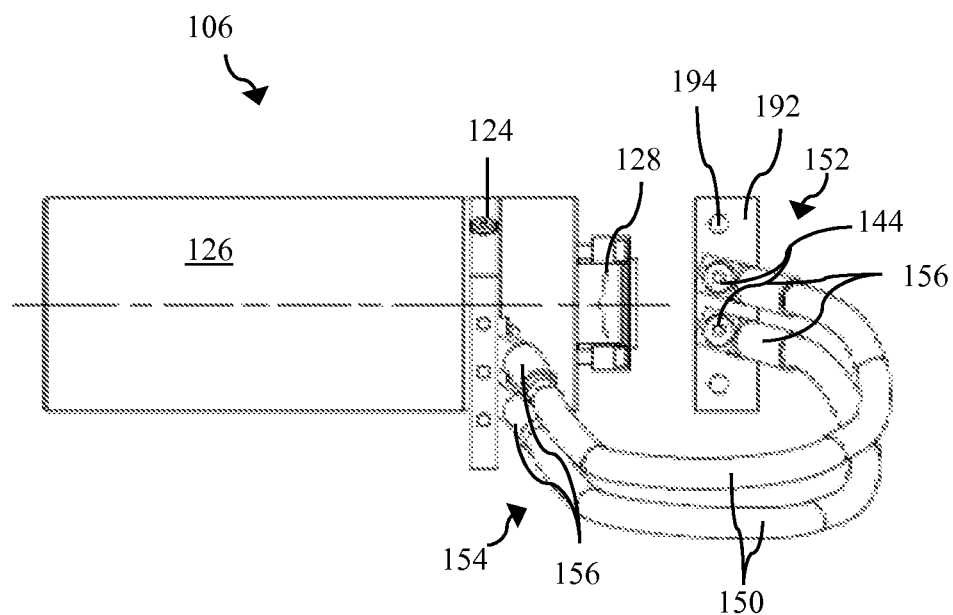
FIG. 11 shows a side view of a second compression anvil assembly including a heating current by-pass system as shown in FIG. 9, according to embodiments of the invention.
Figure 12:
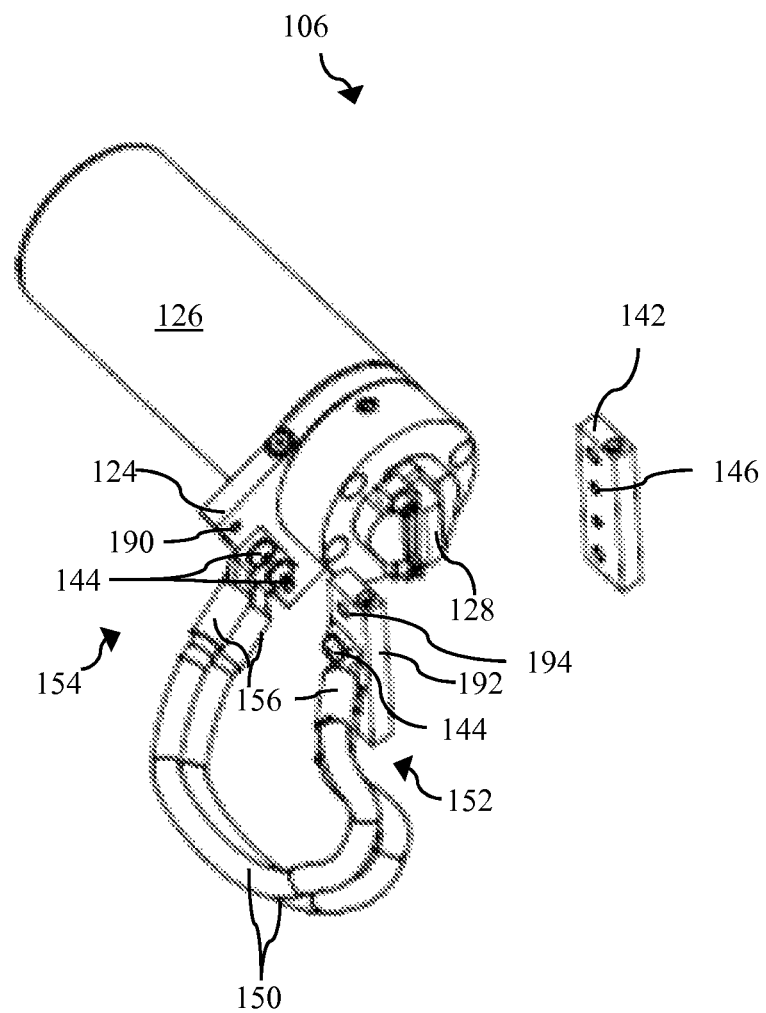
FIG. 12 shows a perspective view of a second compression anvil assembly including a heating current by-pass system as shown in FIG. 9, according to embodiments of the invention.

Turning to FIGS. 5-8, a variety of views of mounting frame 104 including test specimen 118 is shown, according to embodiments of the invention. As shown in FIGS. 5-8, insulating connectors 120 may be substantially cylindrical rods of insulated material coupled to each end of the set of conductive end plates 114. More specifically, as shown in FIG. 5, insulating connectors 120 may be coupled to each end of the set of conductive end plates 114 using an adjustable connection assembly 166. As shown in FIG. 5, adjustable connection assembly 166 may positioned concentrically through insulating connectors 120 for coupling insulating connectors 120 to the set of conductive end plates 114. Adjustable connection assembly 166 may include an extension spring 168, an anchor stud 170 coupled to each end of extension spring 168 and a nut 172 coupled to each end of anchor stud 170. As shown in FIGS. 5-8, extension spring 168 may be positioned substantially through insulating connectors 120, and one of the plurality of apertures 148 formed on each of the set of conductive end plates 114. Additionally, as shown in FIGS. 5-8, a portion of anchor stud 170 may be substantially positioned through the plurality of apertures 148 formed on each of the set of conductive end plates 114, and may include nut 172 positioned outside one of the plurality of apertures 148 and substantially adjacent the set of conductive end plates 114. Adjustable connection assembly 166 may allow the set of conductive end plates 114 to move in an axial direction during a simulation of test specimen 118, as discussed herein. More specifically, as force is applied to test specimen 118 by first compression anvil 110 and second compression anvil 128 (FIGS. 1 and 2), test specimen 118 may expand between the set of conductive end plates 114. As such, adjustable connection assembly 166, and particularly extension spring 168 may allow the set of conductive end plates 114 to expand with test specimen 118 during a simulation, as discussed herein.

In various embodiments, as shown in FIGS. 5-8, a plurality of mounting components 122 may be pivotally coupled to insulating connectors 120 of mounting frame 104, adjacent the ends of insulating connectors 120 coupled to conductive end plates 114. More specifically, as shown in FIGS. 5-8, insulating connectors 120 may be concentrically positioned within an opening 174 of each of the plurality of mounting components 122, such that insulating connectors 120 may rotate within mounting components 122. In an embodiment, as shown in FIG. 5, snap rings 176 and insulating bushings 178 may also positioned within opening 174 of each of the plurality of mounting components 122 to aid in the rotation of insulating connectors 120.

As shown in FIGS. 5-8, test specimen 118 may be coupled to mounting frame 104 by positioning a screw 180 through apertures 182 of test specimen 118 in alignment with openings 184 of each of the set of conductive end plates 114. That is, when test specimen 118 is positioned on the set of conductive end plates 114 in preparation for a simulation, apertures 182 of test specimen 118 and openings 184 of the set of conductive end plates 114 may be in alignment for receiving screw 180 to couple test specimen 118 to conductive end plates 114 of mounting frame 104. Mounting frame 104 may also include specimen clips 186 positioned between screw 180 and test specimen 118. More specifically, specimen clips 186 may be coupled to second contact surface 130 of test specimen 118, and may include an opening 188 for receiving screw 180 to couple test specimen 118. Specimen clips 186 may be used within mounting frame 104 to substantially ensure even contact of test specimen 118 to the set of conductive end plates 114. Additionally, specimen clips 186 may be substantially "L-shaped," for substantially preventing the shifting or rotation of test specimen 118 during a simulation, where test specimen 118 deforms in shape and/or screws 180 are loosened.

Turning to FIGS. 9-12, a variety of views of the second compression anvil assembly 106 including heating current by-pass system 132 is shown according to embodiments of the invention. As shown in FIGS. 9-12, and as discussed herein, second compression anvil assembly 106 may include conductive mounting plate 124 coupled to mounting shaft 126, second compression anvil 128 coupled to conductive mounting plate 124, and heating current by-pass system 132 coupled to conductive mounting plate 124 and one of the set of conductive end plates 114 of mounting frame 104 (FIGS. 1 and 2). In an embodiment, as shown in FIGS. 9-12, second compression anvil 128 of second compression anvil assembly 106 may be configured as a water cooled compression anvil, similar to first compression anvil 110 (FIGS. 3 and 4), discussed herein. As shown in FIGS. 9-12, conductive mounting plate 124 may include a plurality of openings 190 disposed through conductive mounting plate 124. The plurality of openings 190 may be used for coupling heating current by-pass system 132 to conductive mounting plate 124. Conductive mounting plate 124 may be made from copper, or any other metal having substantially similar conductivity properties as copper.

As shown in FIGS. 9-12, heating current by-pass system 132 may be coupled to conductive mounting plate 124 and one of the set of conductive end plates 114 of mounting frame 104 (FIGS. 1 and 2), in a similar fashion as previously discussed with reference to heating current ground system 112 of first compression anvil assembly 102 (FIGS. 3-4). That is, heating current by-pass system 132 of second compression anvil assembly 106 may include a current plate 192, substantially similar to ground plate 142 of heating current ground system 112. Current plate 192 may be coupled to one of the set of conductive end plates 114 of mounting frame 104 (FIG. 1). More specifically, current plate 192 may be coupled to one of the set of conductive end plates 114, and ground plate 142 of heating current ground system 112 may be coupled to the other of the set of conductive end plates 114. As discussed herein, current plate 192 and ground plate 142 may form an electric current connection through test specimen 118. As shown in FIGS. 1 and 9-12, and as previously discussed, current plate 192 may be coupled to one of the set of conductive end plates 114 by positioning screw 144 within one of the plurality of apertures 194 formed on current plate 192, and one of the plurality of apertures 148 formed on the set of conductive end plates 114. Briefly returning to FIG. 1, current plate 192 of heating current by-pass system 132 may substantially contact test specimen 118 to provide an electric current connection between current plate 192 and test specimen 118. In an alternative embodiment, current plate 192 may be coupled to one of the set of conductive end plates 114 by any conventional mechanical coupling technique, e.g., fastening, welding, brazing, bolting, etc.

Returning to FIGS. 9-12, heating current by-pass system 132 of second compression anvil assembly 106 may also include at least one conductive cable 150, as similarly described with reference to heating current ground system 112. As shown in FIGS. 9-12, and similar discussed with reference to FIGS. 3-4, the at least one conductive cable 150 may include a first end 152 coupled to current plate 192, and a second end 154 coupled to conductive mounting plate 124. More specifically, first end 152 and second end 154 of the at least one conductive cable 150 of heating current by-pass system 132 may include crimp lug 156 for coupling the at least one conductive cable 150 to the respective components (e.g., conductive mounting plate 124) of second compression anvil assembly 106. As shown in FIGS. 9-12, screw 144 may be positioned within crimp lug 156 for coupling first end 152 to conductive plate 192 and second end 154 to conductive mounting plate 124, respectively.

The at least one conductive cable 150, as shown in FIGS. 9-12, may be coupled to current plate 192 and conductive mounting plate 124 to form an electric current connection between current plate 192 and conductive mounting plate 124. More specifically, as discussed herein, the at least one conduction cable 150 may be coupled to current plate 192 and conductive mounting plate 124 in order to provide an electric current ground for TMTA 100 (FIGS. 1 and 2). The at least one conduction cable 150 may include a flexible copper cable capable of transferring a heating current through TMTA 100, as discussed herein. In an alternative embodiment, the at least one conductive cable 150 may be coupled current plate 192 and/or conductive mounting plate 124 by any conventional mechanical coupling technique, e.g., fastening, welding, brazing, bolting, etc.

Figure 13:
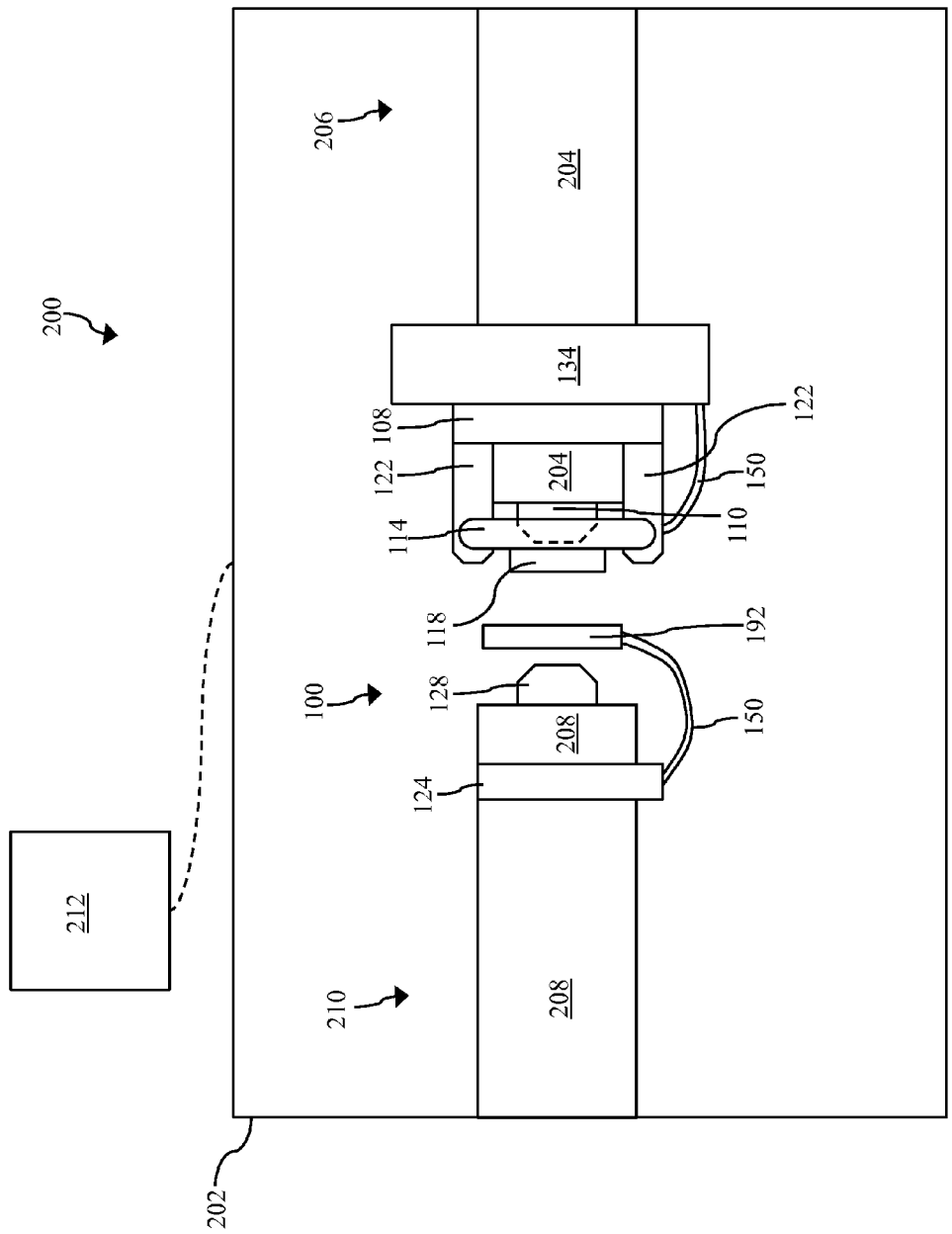
FIG. 13 shows a schematic depiction of a electrically conductive specimen testing system including a thermal-mechanical testing apparatus, according to embodiments of the invention.

Turning to FIG. 13, a schematic depiction of a electrically conductive specimen testing system 200 is shown including TMTA 100, according to embodiments of the invention. As shown in FIG. 13, electrically conductive specimen testing system (MSTS) 200 may include a housing 202, a first mounting shaft 204 positioned within housing 202 on a first side 206, and a second mounting shaft 208 positioned within housing 202 on a second side 210, opposite first side 206. That is, first mounting shaft 204 and second mounting shaft 208 may be positioned opposite one-another within housing 202, such that first mounting shaft 204 and second mounting shaft 208 may move toward each other during a simulation performed by MSTS 200. As shown in FIG. 13, MSTS 200 may also include TMTA 100 coupled to first mounting shaft 204 and second mounting shaft 208, respectively. More specifically, as shown in FIG. 13, first compression anvil assembly 102 may be coupled to first mounting shaft 204, and second compression anvil assembly 106 may be coupled to second mounting shaft 208 for performing a simulation on test specimen 118, as discussed herein. That is, first mounting shaft 204 and second mounting shaft 208, may be configured to move toward one another, for applying a compression force on test specimen 118 of TMTA during a simulation performed by MSTS 200, as described herein. Briefly returning to FIGS. 1-4, first mounting shaft 204 may be similar to mounting shaft 138 and second mounting shaft 208 may be similar to mounting shaft 126, as discussed herein.

MSTS 200 may also include a control system 212 in electronic communication with MSTS 200. Control system 212 may be configured as any conventional data processing system (e.g., computer system) capable of receiving, temporarily storing and transmitting/forwarding data within the system and to external components coupled to the system (e.g., first mounting shaft 204, second mounting shaft 208, heating current by-pass system 132, etc.). More specifically, control system 212 may be configured as any conventional hardware device (computer system controller), and the components of control system 212 (not shown) may be configured as software components stored within said computer system forming control system 212. Control system 212 may aid in performing the simulation on test specimen 118 using MSTS 200, and monitoring the results of the simulation, as discussed herein.

MSTS 200, as shown in FIG. 13, may include a Mobile Conversion Unit (MCU) created by Dynamic System Inc.™ (DSI) of Poestenkill, N.Y., that may utilize TMTA 100 within one of DSI's commercial simulation systems. More specifically, TMTA 100 may be utilized in an illustrative simulator such as MSTS 200, or the "Gleeble" and "Hydrawedge II" systems manufactured by DSI, which is the present assignee hereof (with "Gleeble" and "Hydrawedge II" being registered trademarks owned by DSI). These illustrative simulators or system may perform a simulation on test specimen 118 as described herein, and may receive data relating to the simulation to be utilized in a full scale fabrication process that is substantially simulated by the simulation on test specimen 118.

With reference to FIGS. 1, 2 and 13, a method for performing a simulation on test specimen 118 is now discussed. The simulation on test specimen 118 described herein may simulate a fabrication process performed on the same material that makes-up test specimen 118. More specifically, the simulation described herein may relate to fabrication processes including, but not limited to, multi-stand roll milling and/or multi-hit forging of a material. The method for performing the simulation may include providing TMTA 100 within a MSTS 200, as shown in FIG. 13. MSTS 200 and TMTA 100 may include all components (e.g., first compression anvil assembly 102, mounting frame 104, second compression anvil assembly 106, first and second mounting shafts 204, 208, etc.) as previously discussed herein. As such, further explanation is omitted for clarity.

Once TMTA 100 is provided in MSTS 200, and specifically, test specimen 118 is coupled to mounting frame 104, and is positioned between first compression anvil 110 and second compression anvil 128, test specimen 118 may be continuously heated. More specifically, a contact area of first contact surface 116 and second contact surface 130 of test specimen 118 may be heated using heating current by-pass system 132 of second compression anvil assembly 106 and heating current ground system 112 of first compression anvil assembly 102. While the entire test specimen 118 may be continuously heated, MSTS 200 may be heating the contact area of test specimen 118 to a desired temperature for accurately simulating the fabrication process. The contact area may be central portion of test specimen 118 spanning the entire contact surface (e.g., first contact surface 116) of test specimen 118 and a length substantially wider than the contact area of first compression anvil 110 and second compression anvil 128. That is, the contact area may include a heated portion of test specimen 118 that includes an area substantially larger than a contact area of first compression anvil 110 and second compression anvil 128. Test specimen 118 may be continuously heated by passing an electric current through test specimen 118, and along an electric current connection path formed within TMTA 100. More specifically, test specimen 118 may be heated by passing an electric current from heating current by-pass system 132 of second compression anvil assembly 106 to heating current ground system 112 of first compression anvil assembly 102. As discussed herein, an electric current connection path may be formed by heating current by-pass system 132, test specimen 118 and heating current ground system 112. That is, an electric current may be passed from conductive mounting plate 124 to current plate 192 via the at least one conductive cables 150 of heating current by-pass system 132. Current plate 192, coupled to one of the set of conductive end plates 114, receives the electric current and passes the current to one of the set of conductive end plates 114, which may then send the current through test specimen 118. The other of the set of conductive end plates 114 may receive the electric current from test specimen 118, and may transfer the current to ground plate 142 of heating current ground system 112 coupled thereto. Ground plate 142 may then transfer, or ground, the electric current to mounting plate 108 of first compression anvil assembly 102 via the at least one conductive cables 150 of heating current ground system 112. As the electric current flow through test specimen 118, it may substantially focus the majority of the current on the central portion of test specimen 118 to create the desired contact area of test specimen 118 for simulation.

After the test specimen 118 is heated to a desired temperature, and more specifically, the contact area is formed on the central portion of test specimen 118, first compression anvil 110 of first compression anvil assembly 102 may contact first contact surface 116 of test specimen 118 and second compression anvil 128 may contact second contact surface 130 of test specimen 118 for performing the simulation. That is, first mounting shaft 204 and second mounting shaft 208 may move the respective anvils (e.g., first compression anvil 110, second compression anvil 128) toward one another to engage the anvils against the contact area of test specimen 118. In an embodiment, first mounting shaft 204 and second mounting shaft 208 may be moved and engage test specimen 118 with a predetermined compression force to perform the desired simulation using MSTS 200.

As first compression anvil 110 and second compression anvil 128 engage test specimen 118 and apply a compression force against the contact area of test specimen 118 during the simulation, test specimen 118 may continue to be heated. More specifically, an electric current may continuously be passed through test specimen 118 to maintain a desired temperature during the simulation. As a result of continuously heating test specimen 118 during the simulation, TMTA 100 may substantially reduce the risk of temperature loss in test specimen 118 that may be caused by the (water-cooled) first compression anvil 110 and second compression anvil 128, which may improve the received result of the simulation on test specimen 118.

Additionally, as discussed herein, when first compression anvil 110 and second compression anvil 128 engage test specimen 118, mounting frame 104 may self-align, to position test specimen 118 substantially perpendicular to first compression anvil 110 and second compression anvil 128, respectively. That is, the set of insulating connectors 120 pivotally coupled to mounting components 122 may rotate, causing the set of conductive end plates 114, and ultimately test specimen 118 to align itself substantially perpendicular to first compression anvil 110 and second compression anvil 128.

Furthermore, as first compression anvil 110 and second compression anvil 128 engage and apply a compression force against the continuously heated test specimen 118, test specimen 118 may expand in an axial direction between the set of conductive end plates 114. As discussed herein, adjustable connection assembly 166 may allow for compensation of the expansion of test specimen 118 within the mounting frame 104. More specifically, adjustable connection assembly 166 may allow the set of conductive end plates 114 to expand in an axial direction with test specimen 118, and may maintain a connection between insulating connectors 120 and the set of conductive end plates 114 via, at least in part, extension spring 168.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A thermal-mechanical materials testing apparatus comprising:
    a first compression anvil assembly including:
        a mounting plate;
        a first compression anvil coupled to the mounting plate; and
        a heating current ground system coupled to the mounting plate;
    a mounting frame coupled to the first compression anvil assembly, the mounting frame including:
        a set of conductive end plates for positioning a first contact surface of a test specimen adjacent the first compression anvil of the first compression anvil assembly wherein one of the set of conductive end plates is coupled to the heating current ground system;
        a set of insulating connectors connecting the set of conductive end plates;
        and a plurality of mounting components pivotally coupled to the insulating connectors, the plurality of mounting components coupled to the mounting plate of the first compression anvil assembly, wherein the set of insulating connectors is configured to rotate and align the test specimen with respect to the first compression anvil, and permit the test specimen to expand axially in response to a compression force applied from the first compression anvil assembly; and
    a second compression anvil assembly positioned opposite the first compression anvil assembly and the mounting frame, the second compression anvil assembly including:
        a conductive mounting plate;
        a second compression anvil coupled to the conductive mounting plate and positioned adjacent a second contact surface of the test specimen; and
        a heating current by-pass system coupled to the conductive mounting plate connecting to the other of the set of conductive end plates of the mounting frame, and configured to transfer heat to the first contact surface and the second contact surface, wherein the first contact surface has a larger area than a contact area of the first compression anvil, and the second contact surface has a larger area than a contact area of the second compression anvil.

2. The apparatus of claim 1, wherein the heating current ground system of the first compression anvil assembly further includes:
    at least one conductive cable having a first end coupled to the ground plate, and a second end coupled to the mounting plate of the first compression anvil assembly.

3. The apparatus of claim 2, wherein the ground plate of the heating current ground system substantially contacts one of the set of conductive end plates of the mounting frame which substantially contacts the test specimen.

4. The apparatus of claim 1, wherein the heating current by-pass system of the second compression anvil assembly includes one of the following:
    a conductive mounting plate connected to a second mounting shaft;
    a conductive mounting plate connected to the thermal-mechanical materials testing apparatus; or a conductive mounting plate connected to an external heating current source.

5. The apparatus of claim 1, wherein the heating current by-pass system of the second compression anvil assembly further includes:
    a current plate coupled to one of the set of conductive end plates of the mounting frame; and
    at least one conductive cable having a first end coupled to the current plate, and a second end coupled to the conductive mounting plate of the second compression anvil assembly.

6. The apparatus of claim 5, wherein the current plate of the heating current by-pass system substantially contacts one of the set of conductive end plates of the mounting frame which substantially contacts the test specimen.

7. The apparatus of claim 1, wherein the first compression anvil of the first compression anvil assembly is coupled to a first mounting shaft of an electrically conductive specimen testing system.

8. The apparatus of claim 7, wherein the conductive mounting plate of the second compression anvil assembly is coupled to a second mounting shaft of the electrically conductive specimen testing system, the second mounting shaft positioned opposite the first mounting shaft.

9. The apparatus of claim 1, wherein the mounting frame further includes a specimen clip positioned on the set of conductive end plates for securing each end of the test specimen to each of the set of conductive end plates.

10. The apparatus of claim 1, wherein each of the plurality of mounting components is pivotally coupled to the insulating connectors of the mounting frame.

11. The apparatus of claim 1, wherein the mounting frame further includes an extension spring positioned within each of the set of insulating connectors, the extension spring allowing the conductive end plates to substantially expand in an axial direction.

12. The apparatus of claim 1, wherein the mounting frame further includes a compression spring positioned between each of the plurality of mounting components and the mounting plate of the -first compression anvil assembly, the compression spring for substantially separating the mounting frame and the first compression anvil assembly.

13. An electrically conductive specimen testing system comprising:
    a housing;
    a first mounting shaft positioned within the housing on a first side;
    a second mounting shaft positioned within the housing on a second side, opposite the first side; and
    a thermal-mechanical testing apparatus coupled to the first mounting shaft and the second mounting shaft respectively, the thermal-mechanical testing apparatus including:
        a first compression anvil assembly coupled to the first mounting shaft, the first compression anvil assembly having:

a mounting plate;
a first compression anvil coupled to the mounting plate; and
a heating current ground system coupled to the mounting plate;
a mounting frame coupled to the first compression anvil assembly, the mounting frame having:
a set of conductive end plates for positioning a first surface of a test specimen adjacent the first compression anvil of the first compression anvil assembly wherein one of the set of conductive end plates is coupled to the heating current ground system;
a set of insulating connectors connecting the set of conductive end plates; and
a plurality of mounting components pivotally coupled to the insulating connectors, the plurality of mounting components coupled to the mounting plate of the first compression anvil assembly, wherein the set of insulating connectors is configured to rotate and align the test specimen with respect to the first and second compression anvils, and permit the test specimen to expand axially in response to a compression force applied from the first compression anvil assembly; and
a second compression anvil assembly coupled to the second mounting shaft, the second compression anvil assembly having:
a second compression anvil coupled to a second compression anvil positioned adjacent a second surface of the test specimen; and
a heating current by-pass system coupled to a conductive mounting plate connecting to the other of the set of conductive end plates of the mounting frame and including one of the following:
a conductive mounting plate connected to the second mounting shaft;
a conductive mounting plate connected to the thermal-mechanical materials testing apparatus; or a conductive mounting plate connected to an external heating current source;
wherein the heating current by-pass system is configured to heat the first surface and the second surface of the test specimen, the first surface having a larger surface area than the contact area of the first compression anvil and the second surface having a larger surface area than a contact area of the second compression anvil.

14. A method for performing a simulation on a test specimen, the method comprising:
a thermal-mechanical testing apparatus, the thermal-mechanical testing apparatus including:
a first compression anvil assembly including:
a mounting plate;
a first compression anvil coupled to the mounting plate; and
a heating current ground system coupled to the mounting plate;
a mounting frame coupled to the first compression anvil assembly, the mounting frame including:
a set of conductive end plates for positioning a first contact surface of a test specimen adjacent the first compression anvil of the first compression anvil assembly; and wherein one of the set of conductive end plates is coupled to the heating current ground system;
a set of insulating connectors connecting the set of conductive end plates; and
a plurality of mounting components coupled to the insulating connectors, the plurality of mounting components coupled to the mounting plate of the first compression anvil assembly; and
a second compression anvil assembly positioned opposite the first compression anvil assembly and the mounting frame, the second compression anvil assembly including:
a second compression anvil coupled to a conductive mounting plate and positioned adjacent a second contact surface of the test specimen; and
a heating current by-pass system coupled to a conductive mounting plate connecting to the other of the set of conductive end plates of the mounting frame and containing one of the following:
a conductive mounting plate connected to the second mounting shaft;
a conductive mounting plate connected to the thermal-mechanical materials testing apparatus;
or a conductive mounting plate connected to an external heating current source;
continuously heating a first contact area of the first contact surface and a second contact area of the second contact surface of the test specimen using the heating current by-pass system of the second compression anvil assembly, wherein the first contact area is larger than a contact area of the first compression anvil and the second contact area is larger than the second compression anvil; and
engaging the first compression anvil of the first compression anvil assembly against the first contact surface of the test specimen; and
engaging the second compression anvil of the second compression anvil assembly against the second contact surface of the test specimen, wherein the engaging of the first compression anvil and the second compression anvil causes the test specimen to expand in an axial direction.

15. The method of claim 14, wherein the continuously heating of the contact area includes:
passing a current from the heating current by-pass system through the test specimen to the heating current ground system,
wherein the heating current ground system is coupled to the set of conductive end plates of the mounting frame, opposite the heating current by-pass system.

16. The method of claim 14, further comprising:
adjusting the mounting frame in an axial direction to position mounting frame one of: closer, or further from the mounting plate of the first compression anvil assembly.

17. The method of claim 14, further comprising:
adjusting the set of conductive end plates moving in a radial direction during one of:
the continuously heating of the contact area, engaging of the first compression anvil against the first contact surface of the test specimen, or
engaging of the second compression anvil against the second contact surface of the test specimen.

18. The method claim 14, further comprising:
rotating the set of insulating connectors coupled to the plurality of mounting components to substantially position the test specimen in perpendicular alignment with the first compression anvil and the second compression anvil, respectively.

* * * * *